United States Patent
Kudo et al.

(10) Patent No.: US 6,932,798 B2
(45) Date of Patent: Aug. 23, 2005

(54) COLORED ABSORBENT ARTICLE

(75) Inventors: Jun Kudo, Kagawa (JP); Hideki Kondo, Kagawa (JP); Yukihiro Ito, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 262 days.

(21) Appl. No.: 10/340,637

(22) Filed: Jan. 10, 2003

(65) Prior Publication Data

US 2003/0149410 A1 Aug. 7, 2003

(30) Foreign Application Priority Data

Jan. 11, 2002 (JP) .......................... 2002-004215
Aug. 16, 2002 (JP) .......................... 2002-237694

(51) Int. Cl.$^7$ ................................ A61F 13/00
(52) U.S. Cl. .................. 604/385.01; 604/361
(58) Field of Search ............... 604/385.01, 385.03, 604/385.05, 361, 367, 372, 385.14, 378, 387; 2/400, 214; 36/3 B, 44; 137/551

(56) References Cited

U.S. PATENT DOCUMENTS

| | | | | |
|---|---|---|---|---|
| 3,397,697 A | * | 8/1968 | Rickard ....................... 604/370 |
| 3,802,842 A | * | 4/1974 | Lange et al. ................. 436/169 |
| 4,623,340 A | * | 11/1986 | Luceri .................... 604/385.05 |
| 4,801,494 A | | 1/1989 | Datta et al. |
| 5,261,899 A | | 11/1993 | Visscher et al. |
| 5,431,643 A | * | 7/1995 | Ouellette et al. ....... 604/385.05 |
| 5,708,984 A | * | 1/1998 | Shofner ......................... 2/239 |
| 5,766,212 A | * | 6/1998 | Jitoe et al. ................... 604/361 |
| 5,803,920 A | * | 9/1998 | Gilman ....................... 604/378 |
| 6,362,390 B1 | * | 3/2002 | Carlucci et al. ............. 604/367 |

FOREIGN PATENT DOCUMENTS

| | | | |
|---|---|---|---|
| EP | 1 108 406 A2 | 6/2001 | |
| EP | 1 108 406 | 6/2001 | ........... A61F/13/15 |
| EP | 1 174 101 A1 | 1/2002 | |
| EP | 1 247 508 A2 | 10/2002 | |
| EP | 1 250 941 A1 | 10/2002 | |

OTHER PUBLICATIONS

Lindsay et al., "Multicolored Absorbent Articles: A Brief History", Kimberly–Clark Corporation, Neenah, Wisconsin.
Lindsay et al., "Multicolored Absorbent Articles: A Brief History", Oct. 10, 2003, www.priorartdatabase.com/IP-COM/00019928D.

* cited by examiner

Primary Examiner—Larry I. Schwartz
Assistant Examiner—L Hill
(74) Attorney, Agent, or Firm—Darby & Darby (57) ABSTRACT

Disclosed is a colored absorbent article to be attached to an inner side of an undergarment matching in color with the article. The absorbent article has a body surface for facing the skin of a wearer and a garment surface for facing the inner side of the undergarment. A color given to the absorbent article is visually recognizable from the side of the body surface. When measured for the body surface of the absorbent article, a Munsell value is in a range of 5.7 to 8.7.

7 Claims, 2 Drawing Sheets

COLORED ABSORBENT ARTICLE

BACKGROUND OF THE INVENTION

1. Field of the Invention

The present invention relates to an absorbent article suitable for use with an undergarment that matches in color with the article, more particularly, relates to a colored absorbent article that is suitable for use as a panty liner and has an excellent concealability of vaginal discharge and an excellent visibility of menstrual blood.

2. Description of the Related Art

Absorbent articles to be attached to a crotch portion of a woman's undergarment include panty liners that are intended to mainly receive vaginal discharge, as well as sanitary napkins and incontinence pads. Conventional panty liners are intended to absorb a relatively large amount of vaginal discharge so that the vaginal discharge does not leak out of the liner, without giving an unpleasant feeling to the private parts or the skin surrounding the private parts.

In recent years, however, a growing number of users have chosen to wear panty liners even when an amount of vaginal discharge is relatively small. Such users do not wear panty liners for absorption of a large amount of vaginal discharge as in the convention use, but rather wear the liner for stain prevention of undergarments. That is, people who want to keep undergarments clean, take good care of undergarments, or dislike stain on undergarments have chosen to wear panty liners. These people do not wear panty liners as the conventional absorbent article, but mainly intend to use them as a substitute for a crotch portion of an undergarment or an exchangeable crotch portion of an undergarment. In woman's undergarment of late years, a brassiere and panties are integrally designed, and they are usually purchased as a two-piece set or a three-piece set together with a camisole or a slip. However, since the crotch portion of the panties stains easily, the panties, particularly the crotch portion thereof is often washed more carefully as compared with other undergarments or washed with a heavy duty detergent or a bleaching agent. Since the cloth of the panties may be easily exclusively damaged due to repetition of such washing as compared with other undergarments, not a few women purchase spare panties when they purchase undergarments as a two-piece set or a three-piece set. Panty liners are beneficial to such women as a substitute for a crotch portion of an undergarment or an exchangeable crotch portion of an undergarment. By using panty liners everyday, the crotch portion of the panties can be prevented from staining, so that such spare panties are no more required to purchase.

When panty liners are to be used as a substitute for a crotch portion of an undergarment or an exchangeable crotch portion of an undergarment, wearers consider whether or not panty liner is comfortable to wear and whether or not panty liner is felt as an integral part of undergarment, rather than absorbency that has been conventionally regarded as important. Therefore, lighter, thinner and smaller panty liners have become popular. Such panty liners to be used as a substitute for a crotch portion of an undergarment are usually white.

However, a lot of women who stick to undergarment or who take good care of undergarment choose undergarments according to the mood of the day or the schedule of the day (where she goes, who she dates, etc.). Such women regard color of undergarment as important when they choose undergarments. Therefore, a growing number of women have chosen to purchase and wear colored undergarments other than white ones.

Many women who regard color of undergarment as important and take good cure of undergarment have been dissatisfied with white panty liners as a substitute for a crotch portion. More specifically, they have been dissatisfied by the following reasons: an uninteresting, white panty liner has to be used for taking good care of a colored undergarment; only a crotch portion of a colored undergarment becomes white due to a white panty liner; a stain such as vaginal discharge or urine becomes noticeable on the surface of a white panty liner, and a white panty liner attached to a colored undergarment looks as if it is unsanitary because the liner is noticeable due to color difference between the undergarment and the liner and a stain adhered to the liner is also noticeable. In addition, if a white panty liner is attached to a colored undergarment and the colored undergarment is put on or taken off, the attached liner may possibly be noticed.

For example, Patent Publication EP1108406 discloses an absorbent article for such women. This absorbent article is a panty liner having an absorbent core between a topsheet for facing the wearer's skin and a backsheet for facing an undergarment, wherein the topsheet and the backsheet are manufacturered from materials of a dark color such as black. This dark panty liner is less noticeable when attached to a black undergarment. In addition, since the panty liner itself has a dark color, body fluids such as vaginal discharge, urine and menstrual blood, adhered thereto also become less noticeable.

Besides the absorbent article disclosed in the above-identified Publication, a panty liner which is colored green by adding catechin and a panty liner wherein a color given to an absorbent layer or a backsheet can be seen through a topsheet have been on sale, although they are not aimed at matching in color with an undergarment.

The absorbent article disclosed in Patent Publication EP1108405 has a color that matches with a black undergarment and has an effect of concealing body fluids (vaginal discharge, menstrual blood, urine) discharged from the private parts.

In the panty liner having a dark color such as black, body fluids adhered thereto are less noticeable. During a period other than menstruation, therefore, it has an effect of absorbing and concealing vaginal discharge to thereby prevent an undergarment from being stained. However, when a small amount of menstrual blood is adhered thereto immediately after the beginning of menstruation, the dark color may possibly conceal such menstrual blood. In this case, because a wearer cannot notice the beginning of menstruation immediately, she cannot replace the panty liner with a common sanitary napkin timely. As a result, a large amount of menstrual blood that exceeds absorption capacity of the thin panty liner may adhere to the wearer's private parts and surroundings to give her an unpleasant feeling. Furthermore, such menstrual blood may possibly leak out of the panty liner to adhere to not only the undergarment but also outerwear. That is, the panty liner that is intended to prevent the colored undergarment from being stained may lead to menstrual blood stains on the undergarment and the outerwear instead.

In order to prevent this situation, it is possible to increase the absorption capacity of body fluids. In this case, however, because the thickness, weight and area of the panty liner need be increased for increasing the absorption capacity, the panty liner comes to resemble a sanitary napkin or a conventional vaginal discharge absorbing liner. Such a thick, heavy and large panty liner is not suitable for use as a substitute for a crotch portion.

On the other hand, the panty liner colored in green or the like is limited to improvement in its own appearance by making the appearance of the panty liner pale, while concealability of body fluids is inferior because its body surface has a high value. Therefore, although a wearer can notice the beginning of menstruation in an early stage, vaginal discharge cannot be effectively concealed. In addition, since this panty liner is not aimed at matching in color with an undergarment, it is not suitable for use as a substitute for a crotch portion of colored panties.

SUMMARY OF THE INVENTION

The present invention has been worked out in view of the shortcoming in the prior art set forth above. It is therefore an object of the present invention to provide an absorbent article suitable for use with an undergarment that matches in color with the article, wherein vaginal discharge can be effectively concealed and adhesion of menstrual blood can be immediately noticed at the beginning of menstruation.

According to the present invention, there is provided a colored absorbent article to be attached to an inner side of an undergarment matching in color with the article, the absorbent article having a body surface for facing the skin of a wearer and a garment surface for facing the inner side of the undergarment, a color given to the absorbent article being visually recognizable from the side of the body surface, wherein when measured for the body surface of the absorbent article, a Munsell value is in a range of 5.7 to 8.7.

The absorbent article of the present invention has a color other than white. When attached to a crotch portion of an undergarment (e.g., panties) having an analogous or similar color, therefore, the absorbent article becomes less noticeable and looks like an integral part of the crotch portion. In addition, since the value of the body surface is in the above-mentioned range, absorbed vaginal discharge becomes less noticeable, so that an excellent concealability of vaginal discharge can be obtained. When menstruation begins during wear, on the other hand, menstrual blood adhered to the body surface or absorbed can be easily recognized, so that the beginning of menstruation can be sensed in an early stage. Accordingly, the absorbent article of the present invention is suitable for use as a substitute for a crotch portion of an undergarment or an exchangeable crotch portion of an undergarment.

Preferably, the absorbent article comprises a stack of a plurality of sheets, wherein at least one sheet is made of a synthetic resin containing a coloring agent. In such a sheet made of a synthetic resin containing a coloring agent (e.g., a sheet comprising synthetic resin fibers containing a coloring agent, a synthetic resin film containing a coloring agent, or the like), hue and value can be easily adjusted depending on the amount and kind of coloring agent to be contained in the synthetic resin. In addition, since the contained coloring agent never drops from the sheet, it is safe for the human body and can be prevented from adhering to an undergarment. Since the absorbent article is less noticeable when attached to an undergarment, the undergarment may possibly be washed together with the absorbent article. However, since the contained coloring agent never drops from the sheet even when the absorbent article is washed by mistake, the undergarment can be prevented from staining.

Preferably, the absorbent article comprises a topsheet appearing on the body surface and a backsheet appearing on the garment surface, wherein the topsheet and the backsheet are of the substantially same size and colored to have an analogous or similar color. In this case, since the color of the absorbent article can be recognized from both the top and bottom sides, an absorbent article having a color analogous, similar or identical to that of the undergarment can be easily chosen. In addition, the absorbent article is less noticeable even when seen from the outside of the undergarment.

Here, the topsheet and the backsheet may be transversely outwardly protruded to form wing portions of a predetermined area, at a location spaced apart from longitudinally opposed front and rear end edges of the absorbent article. Upon use, the wing portions can be folded back about side edges of a crotch portion of an undergarment and adhered to an outer side of the undergarment so that the absorbent article can be firmly fixed on the undergarment. At this time, since the wing portions on the outer side of the undergarment have a color analogous, similar or identical to that of the undergarment, the wing portions can be made less noticeable.

Preferably, an adhesive layer for adhering to the undergarment is provided on the backsheet such that the adhesive layer is spaced inwardly apart from any edges of the backsheet. In this case, since the adhesive layer is not present in a predetermined region inside the edges of the backsheet, the color of the backsheet is not obscured along the periphery of the backsheet. Therefore, the attached absorbent article is less noticeable. In addition, when the absorbent article is detached from the undergarment, the edge of the absorbent article can be easily taken between the fingers.

Preferably, the absorbent article is of thin type having a thickness of 0.25 to 3.5 mm, between the body surface and the garment surface. In this case, the absorbent article attached to the crotch portion of the undergarment can be felt as an integral part of the crotch portion.

Preferably, the topsheet is a nonwoven fabric. In this case, since the texture of the topsheet becomes analogous to that of a crotch portion of an undergarment that is manufactured from fibers, the absorbent article attached to the crotch portion of the undergarment can be felt as an integral part of the undergarment. In addition, since nonwoven fabric can provide a soft feel to the touch, it can be comfortably worn.

As has been described hereinabove, the absorbent article of the present invention is suitable for use as a panty liner for absorbing vaginal discharge.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
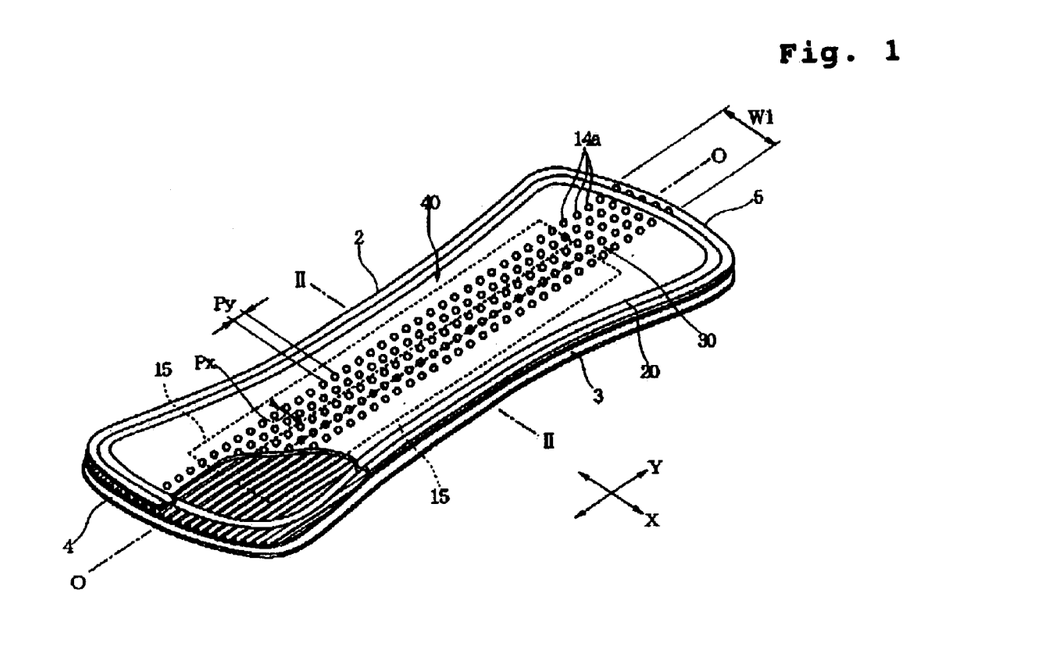
FIG. 1 is a perspective view showing a panty liner according to a first embodiment of the present invention.
Figure 2:
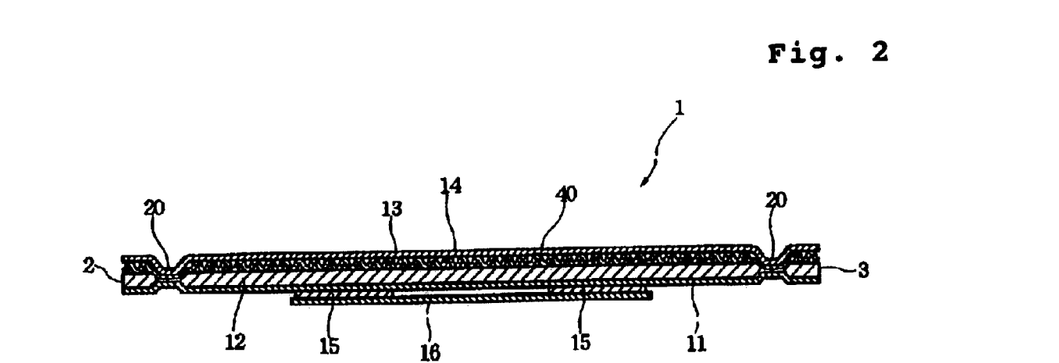
FIG. 2 is a sectional view taken along line II—II of FIG. 1.

FIG. 1 is a perspective view showing a panty liner 1 as a colored absorbent article according to a first embodiment of the present invention; and FIG. 2 is a sectional view of the panty liner 1 taken along line II—II of FIG. 1.

The panty liner 1 of FIGS. 1 and 2 is a thin absorbent article, which is to be worn by women while being attached to an inner side of a crotch portion of an undergarment (e.g., panties) for absorbing body fluids such as vaginal discharge. As used herein, the term "vaginal discharge" refers to a small amount of fluid that flows out of the vagina each day, carrying out old cells that have lined the vagina. This discharge is usually clear or milky. It should be noted that the absorbent article and components thereof have two surfaces, of which one surface that is intended to be directed toward the crotch of a wearer is called "body surface," while the other surface that is on the opposite side is called "garment surface".

The panty liner 1 is suitable for use with an undergarment that matches in color with the panty liner 1. In other words, a panty liner 1 of a color that is analogous, similar or identical to that of an undergarment is to be chosen for use. The given color can be recognized as viewed at least from the side of a body surface 40 of the panty liner 1. The term "colored" as used herein refers to a state where a color other than white is given to an object. Therefore, the concept of coloring does not include a state where an object is colored white only with a white pigment or the like.

The panty liner 1 is to be used as a substitute for a crotch portion of an undergarment or an exchangeable crotch portion of an undergarment. For such uses, the panty liner 1 is of thin type of which the thickness is preferably in the range of 0.25 mm to 5 mm, more preferably in the range of 0.5 mm to 3.5 mm. The weight of the panty liner 1 is in the range of 0.5 g to 4 g, preferably in the range of 0.75 g to 3 g, most preferably in the range of 1 g to 2 g. If the thickness and the weight are greater than the above-mentioned upper limits, a wearer tends to feel that something is wrong with an undergarment when such a heavy or thick panty liner is used as a substitute for a crotch portion of the undergarment. If they are less than the above-mentioned lower limits, on the other hand, since the absorption capacity of vaginal discharge and so on decreases, a wearer tends to be afraid that vaginal discharge may not be absorbed by the panty liner. In addition, it is difficult to manufacture such an excessively thin panty liner.

In order that the panty liner 1 attached to a crotch portion of an undergarment can be felt like an integral part of the crotch portion of the undergarment, the maximum longitudinal dimension between front and rear end edges of the panty liner 1 is in the range of 75 mm to 200 mm, preferably in the range of 90 mm to 170 mm, most preferably in the range of 100 mm to 150 mm. On the other hand, the transverse dimension between left and right side edges at a location along or near a transversely extending centerline of the panty liner 1 (where the width of the panty liner becomes the smallest if it is of an hourglass shape, as shown in FIG. 1) is preferably in the range of 30 mm to 80 mm, more preferably in the range of 40 mm to 60 mm, most preferably in the range of 45 mm to 55 mm. Within the above-mentioned range, the panty liner 1 can cover the discharging parts (private parts) of the wearer's body without projecting from a crotch portion of an undergarment.

The entire panty liner 1 preferably has a Gurley stiffness from 10 to 300 mg. The Gurley stiffness is more preferably from 30 to 250 mg, most preferably from 50 to 200 mg. If it is greater than the above-mentioned upper limit, the panty liner 1 attached to the crotch portion of the undergarment may possibly be felt stiff by a wearer. If it is less than the above-mentioned lower limit, the panty liner may possibly be twisted or displaced when the crotch portion of the undergarment is deformed. If it is less than the above-mentioned lower limit, moreover, the panty liner 1 becomes too soft to manufacture.

The Gurley stiffness is expressed by a value measured by using a Gurley flexibility tester: Type 311 manufactured by YASUDA SEIKI SEISAKUSHO LTD. according to the manual attached to the tester. It should be noted that measurement is performed using a test sample having a width of 25.4 mm.

Preferably, nonwoven fabric appears on the body surface 40 of the panty liner 1 as in the following embodiment. In this case, the surface texture becomes analogous to that of the material of the undergarment.

The panty liner 1 of FIG. 1 has right and left side edges 2 and 3 extending in a longitudinal direction (X-direction) and front and rear end edges 4 and 5 extending in a transverse direction (Y-direction). The right and left side edges 2, 3 are inwardly curved and the front and rear end edges 4, 5 are outwardly curved, so that the panty liner 1 is of an hourglass shape as viewed from above.

As shown in FIG. 2, the panty liner 1 is of a laminated structure having four sheets: a liquid-impermeable backsheet 11; an absorbent sheet 12 laid on the backsheet 11 and having an ability to absorb and retain liquid; a liquid-permeable intermediate sheet 13 laid on the absorbent sheet 12; and a liquid-permeable topsheet 14 laid on the intermediate sheet 13.

As viewed from above, the backsheet 11, the absorbent sheet 12, the intermediate sheet 13 and the topsheet 14 are of the same shape and size as the panty liner 1, so that right and left side edges and front and rear end edges of the individual sheets 11, 12, 13 and 14 coincide with the edges 2, 3, 4 and 5 of the panty liner 1, respectively.

After the backsheet 11, the absorbent sheet 12, the intermediate sheet 13 and the topsheet 14 are stacked, the panty liner 1 is formed with a round seal 20 extending continuously along but inwardly spaced 1 to 4 mm apart from the right side edge 2, the left side edge 3, the front end edge 4 and the rear end edge 5. This round seal 20 has a width of about 1 to 3 mm, wherein the four sheets are joined together under pressure using a hot-melt type adhesive or the like.

On a garment surface of the backsheet 11, there is applied a pair of pressure sensitive adhesive layers 15, 15 equally space apart from a longitudinally extending centerline O—O of the panty liner 1. As shown in FIG. 2, a release paper 16 is adhered to a garment surface of the pressure sensitive adhesive layers 15, 15. This release paper 16 is peeled from the pressure sensitive adhesive layers 15, 15 by a wearer of the panty liner 1 to expose the pressure sensitive adhesive layers 15, 15. Then, the panty liner 1 is adhered by applying the pressure sensitive adhesive layers 15, 15 to an inner side of a crotch portion of an undergarment. Thus, the panty liner 1 is used as a part of (substitute for) a crotch portion of an undergarment.

As shown in FIG. 1, the topsheet 14 is formed with liquid passage holes 14a that are dotted over a region having a constant width W1 and extending along the centerline O—O over the entire length of the topsheet 14. The region having the liquid passage holes 14a is called "central liquid passage region 30".

In the central liquid passage region 30, the liquid passage holes 14a are regularly arranged. Each liquid passage hole 14a is of a circular shape. Both a longitudinal pitch Py and a transverse pitch Px of the liquid passage holes 14a are in the range of 2 to 5 mm. An opening diameter of the liquid passage hole 14a is about 0.5 to 3 mm on a plane flush with the body surface of the topsheet 14. The area ratio of the liquid passage holes 14a to the central liquid passage region 30 is in the range of 8 to 20%.

The width W1 of the central liquid passage region 30 in which the liquid passage holes 14a are uniformly distributed is preferably in the range of 10 to 30 mm. Within the above-mentioned range, the vaginal opening of a wearer can be certainly covered with the central liquid passage region 30, so that body fluids such as vaginal discharge can be received mainly by the central liquid passage region 30.

These liquid passage holes 14a can be formed by subjecting the topsheet 14 to a secondary mechanical process. With the liquid passage holes 14a thus formed, the texture of the body surface 40 of the panty liner 1 becomes analogous to that of a crotch portion of a undergarment, so that the panty liner 1 can be felt as an integral part of the crotch portion of the undergarment. In an alternative, the topsheet 14 may be corrugated (similar to the intermediate sheet 13 that will be described in detail later) in a secondary mechanical process. In another alternative, the topsheet 14 may be pin-embossed to have a large number of recesses. Such a corrugated topsheet 14 is suitable for use as a substitute for a crotch portion of an undergarment because it can provide not only a soft feel to the touch but also an appearance analogous to that of cloth.

The intermediate sheet 13 is corrugated to have ribs and valleys extending in the longitudinal direction. These ribs and valleys are arranged such that a peak-to-peak distance between adjacent ribs is about 1 to 3 mm. The thickness of the corrugated intermediate sheet 13 (i.e., a distance between the garment surface of the intermediate sheet 13 at a location where the bottoms of the valleys are in contact with the absorbent sheet 12 and the body surface of the intermediate sheet 13 at a location where the peaks of the ribs are in contact with the topsheet 14) is from 0.5 to 1.5 mm. If the intermediate sheet 13 is thus corrugated, the panty liner 1 can provide a soft feel when worn.

In the panty liner 1, the topsheet 14 forms the body surface 40. Body fluid such as vaginal discharge given to the body surface 40 and collected by the topsheet 14 mainly passes through the liquid passage holes 14a and then permeates and passes through the intermediate sheet 13. Thus, the body fluid is absorbed and retained by the absorbent sheet 12. The body fluid such as vaginal discharge absorbed and retained by the absorbent sheet 12 is blocked by the liquid-impermeable backsheet 11 so as not to leak out to an undergarment.

As viewed from the side of the body surface 40, the entire panty liner 1 has a color other than white. This color may be pink, light blue, beige or the like, that are analogous, similar or identical to colors that generally suit women's taste about undergarment, so that a wearer can choose one that matches in color with an undergarment intended to be worn.

When measured for the body surface 40 of the finished panty liner 1 in a state where no body fluid such as vaginal discharge is given thereto, a Munsell value is in the range of 5.7 to 8.7. In the embodiment shown, although the body surface 40 is partially processed to have the central liquid passage region 30 dotted with the liquid passage holes 14a, both the value measured for the central liquid passage region 30 and the value measured for the remaining regions of the body surface 40 are in the range of 5.7 to 8.7. Also in the case where the topsheet 14 is corrugated to have ribs and valleys or pin-embossed to have a large number of recesses, values measured for the corrugated region and the pin-embossed region are in the above-mentioned range.

In the case where the Munsell value measured for the body surface 40 of the finished panty liner 1 in a state where no body fluid such as vaginal discharge is given thereto is in the range of 5.7 to 8.7, as set forth above, there is little difference between a value of vaginal discharge and the value of the body surface 40 of the finished panty liner 40, so that the color of vaginal discharge adhered to the body surface 40 or having reached to the intermediate sheet 13 or the absorbent sheet 12 via the topsheet 14 can be made less noticeable.

On the other hand, since a value of menstrual blood is significantly different from the value of the body surface 40 of the finished panty liner 1, menstrual blood adhered to the body surface 40 or having reached to the intermediate sheet 13 or the absorbent sheet 12 via the topsheet 14 can be visually recognized immediately. Therefore, even when menstruation begins during wear of the panty liner 1, the beginning of menstruation can be sensed by a wearer in an early stage, so that a wearer can replace the panty liner 1 with a sanitary napkin in an early stage after the beginning of menstruation. Therefore, menstrual blood can be effectively prevented from being given to the panty liner 1 in an amount in excess of the absorption and retention capacity of the panty liner 1, leaking out of it, and blotting an undergarment and so on.

As used herein, the "Munsell color system" refers to the Renotation Munsell system that is the color specification system created by Albert H. Munsell and then revised by the Colorimetric Committee of the Optical Society of America.

According to the Munsell color system, color is expressed by three attributes Hue, Value, and Chroma. The "Hue" means the attribute of color which can be found in the spectrum of light. In the Munsell color system: red (R), yellow (Y), green (G), blue (B), and purple (P) are selected as five principle hues; and yellow-red (YR), green-yellow (GY), blue-green (BG), purple-blue (PB), and red-purple (RP) are arranged therebetween as five intermediate hues. In these ten hues, degree of each hue is expressed in equally spaced relation such that the maximum degree of each hue is 10. The "Value" means the attribute of visual sensation which can express the magnitude of luminous reflectance (reflectance with respect to lightness) of an object surface. In the Munsell color system, the value is expressed in equally spaced relation such that black that can completely absorb light is 0 and white that can completely reflect light is 10. The "Chroma" means sharpness of color. In the Munsell color system, achromatic color is 0 and the numerical value increases in equally spaced relation as the sharpness increases.

As used herein, the "analogous color" means a range of hue within ±5 degrees. For example, an analogous color with respect to 5B is in the range of 10B to 10BG. On the other hand, the "similar color" means a range of hue within ±2.5 degrees. For example, a similar color with respect to 5YR is in the range of 2.5YR to 7.5YR.

Hue, value and chroma can be determined by using a measuring device. In the present invention, hue, value and chroma are determined by using a colorimeter (CR-300) manufactured by MINOLTA Co., Ltd.

The value of the body surface 40 of the panty liner 1 can be set within the range of 5.7 to 8.7 as long as at least one of the topsheet 14, the intermediate sheet 13, the absorbent sheet 12 and the backsheet 11 forming the panty liner 1 is colored. In the panty liner 1 of this embodiment, however, the backsheet 11 is colored to have an analogous or similar color to that of the topsheet 14. In this case, it is preferred that the value of the garment surface of the panty liner 1 (i.e., the value measured from the side of the backsheet 11) is also set within the range of 5.7 to 8.7.

If the backsheet 11 is colored to have an analogous or similar color (preferably an identical color) to that of the topsheet 14 and both values of the topsheet 14 and the backsheet 11 are in the range of 5.7 to 8.7, both the body surface and the garment surface of the panty liner 1 can match in color with an undergarment. When attached to a crotch portion of the undergarment, therefore, the panty liner 1 can look like an integral part of the crotch portion of the undergarment. In addition, even if a part of the panty liner 1 projects from the crotch portion, it is less noticeable that the panty liner 1 is worn.

Hue of the panty liner 1 can be arbitrarily set except for white. In order that the body surface has a value in the range of 5.7 to 8.7, however, hue for pink type is preferably set in the range of 5RP to 5R, hue for light blue type is preferably set in the range of 5BG to 10B, and hue for beige type is preferably set in the range of 5YR to 10YR (each range is a clockwise range in the Munsell hue circle) With the hue being set within the range, the value can be easily set within the range of 5.7 to 8.7.

As has been described hereinabove, the pressure sensitive adhesive layers 15 are disposed on the garment surface of the backsheet 11. Such pressure sensitive adhesive layers 15 are preferably spaced at least 2 mm apart from any edges of the backsheet 11. If the pressure sensitive adhesive layers 15 are thus provided, the color of backsheet 11 is not obscured by the pressure sensitive adhesive layers 15 in a predetermined peripheral region along the edges. Therefore, even in case where the side edges of the backsheet 11 project from a crotch portion of an undergarment, they are less noticeable from the outside. Also in case where the front end edge 4 or the rear end edge 5 of the panty liner 1 is folded back against the body surface, the panty liner 1 remains still less noticeable from the inside of an undergarment, because the color of the panty liner 1 that is analogous or similar to that of the undergarment is not affected. If the pressure sensitive adhesive layers 15 are thus spaced apart from any edges of the backsheet 11, moreover, any edges of the panty liner 1 can be taken between the fingers, so that the panty liner 1 can be easily removed from the crotch portion of the undergarment.

The topsheet 14 and/or the intermediate sheet 13 may be formed of spunbonded nonwoven fabric, of which at least part of constituent fibers are made of a synthetic resin mixed with a coloring agent. In order to uniformly color the surface of the nonwoven fabric, it is preferred that all the constituent fibers of the nonwoven fabric are fibers thus colored.

Here, the topsheet 14 and/or the intermediate sheet 13 may be of a multi-layer structure, wherein two nonwoven fabrics may be partially thermal-bonded together or bonded together through an adhesive. In this case, one layer for facing the wearer's body may be a nonwoven fabric comprising colored fibers; the other layer for facing an undergarment may be formed of uncolored fibers. In an alternative, three nonwoven fabrics may be joined together as set forth above into a multi-layer structure, wherein two outer layers may be nonwoven fabrics comprising colored fibers; an intermediate sheet may be formed of uncolored fibers.

The colored synthetic fibers may be formed by melt extruding a mixture of a pellet of a synthetic resin such as polypropylene resin and a masterbatch comprising a coloring agent and a synthetic resin such as polypropylene resin. Other kinds of nonwoven fabric such as spunlaced nonwoven fabric comprising the colored synthetic resin fibers may also be used.

If the topsheet 14 is formed of nonwoven fabric, the texture of the body surface 40 of the panty liner 1 can be made similar to that of a crotch portion of an undergarment.

In an alternative, a colored resin film formed by melt extruding a mixture of a pellet of a synthetic resin such as polyethylene resin or polypropylene resin and a masterbatch comprising a coloring agent and a synthetic resin such as polyethylene resin or polypropylene resin, followed by processing it to have apertures, may be used as the topsheet 14. Here, it is also possible to join the colored resin film to the nonwoven fabric of the colored fibers or join the colored resin film to a nonwoven fabric of uncolored fibers.

For the topsheet 14, it is also possible to color at least one surface of a sheet (e.g., nonwoven fabric comprising synthetic resin fibers, apertured resin film or the like) by printing. Here, printing may be performed by flexographic printing, gravure printing, ink jet printing or the like. Among them, most preferred is flexographic printing. Because no organic solvent is used, flexographic printing is remarkably safe for the human body. Here, since gravure printing tends to apply large tension to nonwoven fabric or resin film, uniform and stable printing is difficult. On the other hand, since flexographic printing is performed with nonwoven fabric or resin film laid on a drum, no large tension is given to nonwoven fabric or resin film, so that it is possible to stably fix ink without displacement. Printing techniques other than flexographic printing and gravure printing are not suitable for mass production due to their high cost. When nonwoven fabric or resin film is colored by printing, it is preferred to choose a highly safe ink such as edible food ink.

For the backsheet 11, preferably used is a colored resin film which can be made of the colored polyethylene resin or the like. In this case, the colored resin film is preferably made moisture-permeable (breathable) by adding inorganic filler or the like to the pellet of a synthetic resin and the masterbatch containing a coloring agent, melt extruding these materials into a film, and then drawing the film to have a large number of pores. It is also possible to use a spunbond-meltblown-spunbond (S-M-S) laminate of which at least one layer of nonwoven fabric comprises colored synthetic resin fibers.

For the absorbent sheet 12, preferably used is spunlaced nonwoven fabric comprising rayon that is regenerated cellulose fibers, polyethylene terephthalate fibers and polypropylene fibers. In the absorbent sheet 12, the constituent fibers are white or have natural colors of individual fibers. However, it is also possible that the constituent fibers are given a color other than white.

For the absorbent sheet 12, also usable are an air-laid nonwoven fabric containing pulp, the air-laid and superabsorbent polymer, pulp and superabsorbent polymer, and a superabsorbent polymer sheet. In the case where superabsorbent polymer is used, however, menstrual blood given to the panty liner 1 may possibly be missed due to superior absorbency of superabsorbent polymer. In addition, since the panty liner 1 becomes stiff due to superabsorbent polymer, it cannot be comfortably worn as a substitute for a crotch portion of an undergarment. In order to reduce such stiffness, superabsorbent polymer need be used together with soft materials such as pulp, so that the resulting panty liner becomes thick and inappropriate for a substitute for a crotch portion. Furthermore, if detachment of the panty liner before washing an undergarment is forgotten, superabsorbent polymer absorbs water used for washing, possibly causing trouble in washing.

As has been described hereinabove, at least one sheet of the topsheet 14, the intermediate sheet 13, the absorbent sheet 12 and the backsheet 11 is required to be colored in order to provide the panty liner 1 with a color of predetermined hue and value. If such a colored sheet is manufactured from a synthetic resin containing a coloring agent, hue and value can be easily adjusted depending on the amount and kind of coloring agent. In addition, since the coloring agent thus added hardly drops off, the panty liner can be felt safe for the human body and hardly causes a problem of changing color of an undergarment. The coloring agent hardly drops off even if the panty liner is washed together with an undergarment by mistake.

The individual sheets 11, 12, 13 and 14 may be prepared as water-disintegratable sheet comprised of colored biodegradable materials. In this case, when the panty liner after use is disposed of in a flush toilet, fibers of the water-disintegratable sheet can be dispersed in water and then biodegraded, thereby preventing function damage to septic tank and sewage system as well as preventing deterioration of environment. As used herein, the term "biodegradable" means that fibers can be broken down within a living body or by bacteria. The term "water-disintegratable" means that when a sheet is put in water, constituent fibers of the sheet can be dispersed. The water-disintegratable sheet comprised of biodegradable materials may be spunlaced nonwoven fabric formed of natural fibers such as pulp fibers, regenerated cellulose fibers, purified cellulose fibers or combinations thereof, wherein at least part of fibers are colored.

In the shown embodiment, the panty liner 1 is illustrated as having four layers (i.e., the topsheet 14, the intermediate sheet 13, the absorbent sheet 12 and the backsheet 11). However, the present invention should not be limited thereto, but may be of other structures as long as Munsell value of the body surface of the finished panty liner is in the range of 5.7 to 8.7. For example, the panty liner may be of three-layer structure without providing the intermediate sheet 13. If the topsheet 14 is formed of a thick material having an ability to absorb and retain liquid, the panty liner may be of two-layer structure having the topsheet 14 and the backsheet 11 or a single-layer structure having the topsheet 14 alone. It is also possible to provide two or more intermediate sheets.

In the shown embodiment, the topsheet 14 is illustrated as having the central liquid passage region 30 over which the liquid passage holes 14a are dotted, but the present invention should not be limited thereto. For example, the liquid passage holes 14a may not be formed as long as Munsell value of the body surface of the finished panty liner is in the range of 5.7 to 8.7. It is also possible to subject the topsheet 14 to other secondary mechanical processes for forming corrugation or the like as long as Munsell value is in the above-mentioned range.

The intermediate sheet 13 may not be corrugated as long as Munsell value is in the above-mentioned range.

Figure 3:
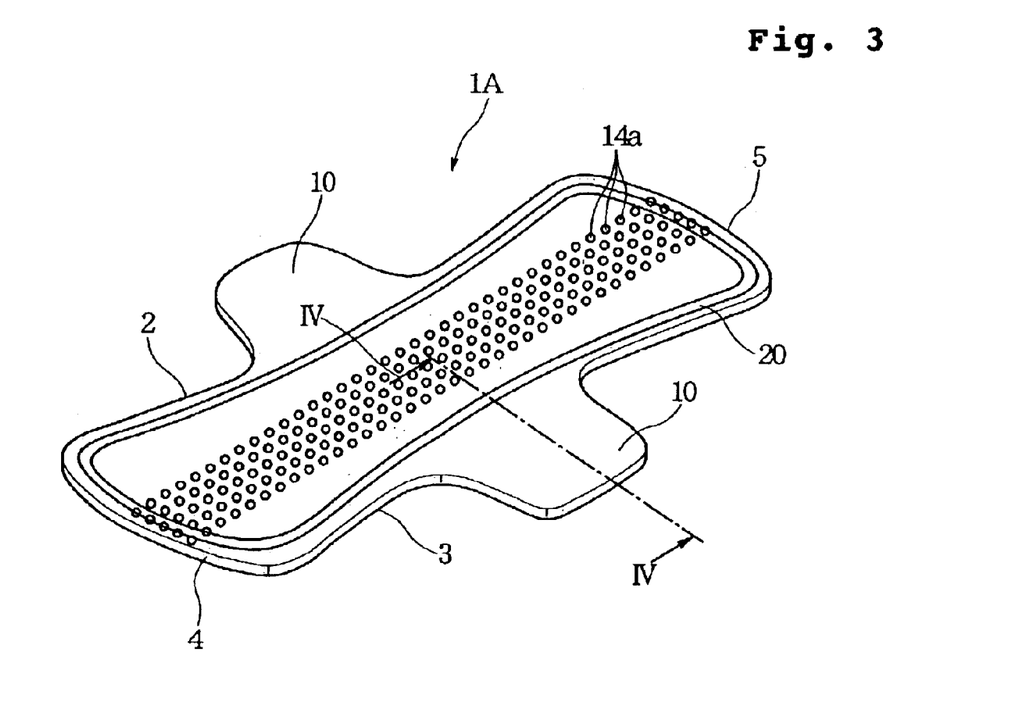
FIG. 3 is a perspective view showing a panty liner according to a second embodiment of the present invention.
Figure 4:
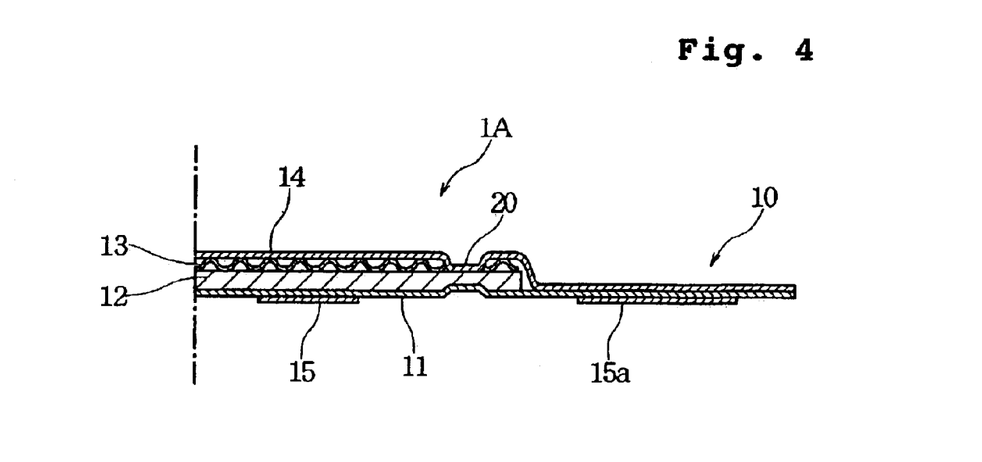
FIG. 4 is a half-sectional view taken along line IV—IV of FIG. 3.

FIG. 3 is a perspective view showing a panty liner 1A as an absorbent article according to a second embodiment of the present invention; and FIG. 4 is a half-sectional view of the panty liner 1A taken along line IV—IV.

Similar to the panty liner 1, this panty liner 1A is of thin type and intended to be attached to a crotch portion of an undergarment for use so as to mainly absorb vaginal discharge or the like. Here, the detailed description of the portions having the same constructions as those of the panty liner 1 will be omitted by designating them by the common reference numerals.

In the panty liner 1A of FIGS. 3 and 4, the right and left side edges 2 and 3 are transversely outwardly protruded to form wing portions 10, 10, at a location spaced apart from both the front and rear end edges 4 and 5, e.g., at a location near the transversely extending centerline. In the individual wing portions 10, 10, the backsheet 11 and the topsheet 14 are stacked one on another and bonded to each other through a hot-melt type adhesive or the like, as shown in FIG. 4. In the respective wing portions 10, 10, moreover, pressure sensitive adhesive layers 15a, 15a are provided on the garment surface of the backsheet 11.

This panty liner 1A can be certainly fixed on an undergarment such that the pressure sensitive adhesive layers 15, 15 are adhered to an inner side of a crotch portion of the undergarment and then the wing portions 10, 10 are folded back about side edges of the crotch portion and adhered to an outer side of the undergarment through the pressure sensitive adhesive layers 15a, 15a.

In the case where both the topsheet 14 and the backsheet 11 are given an analogous or similar color (preferably, identical color) within the range of 5.7 to 8.7, the body surface and the garment surface of the panty liner 1A including the wing portions 10, 10 can match in color with the undergarment. Therefore, the panty liner attached to the undergarment can be made less noticeable.

EXAMPLES

Concealability of vaginal discharge and visibility of menstrual blood were evaluated with respect to Examples and Comparative Examples.

Examples 1 to 7 and Comparative Examples 1 to 5

In Examples 1 to 7 and Comparative Examples 1 to 5, a first intermediate sheet and a second intermediate sheet were selectively used beneath a topsheet, as shown in Table 1. None of the topsheet, the first intermediate sheet and the second intermediate sheet was processed to have roughness such as corrugation. In addition, these sheets were not formed with liquid passage holes unless otherwise stated.

Example 1

The topsheet, the first intermediate sheet and the second intermediate sheet were stacked one on another. For the topsheet, the first intermediate sheet and the second intermediate sheet, used was spunbonded nonwoven fabric (basis weight: 25 g/m$^2$) that was manufactured from fibers (2.2 dtex) that were obtained by extruding polypropylene (PP) resin into which pink masterbatch (40% by weight of titanium oxide, 0.365% by weight of quinacridone red, 0.135% by weight of condensed azo red, 42.8% by weight of PP resin, 16.7% by weight of dispersing agent) was mixed in an amount of 1.6% by weight.

For the absorbent sheet, used was spunlaced wet-laid nonwoven fabric (basis weight: 38 g/m$^2$) that was manufactured by blending: 55% by weight of 1.39 dtex, 44 mm viscose rayon fibers; 30% by weight of 1.44 dtex, 38 mm polyethylene terephthalate (PET) fibers; and 15% by weight of 1.67 dtex, 45 mm polypropylene (PP) fibers, and hydroentangling them. Any coloring agents having a color other than white were not used in the materials of the absorbent sheet. The viscose rayon had a natural color that was not changed from the color at the time of manufacturing, while the PET and PP fibers were whitened due to inorganic filler added thereto. Hue and value measured for the absorbent sheet alone were identical to those of the absorbent sheet in Examples 8 and 9. The same spunlaced nonwoven fabric was used for the absorbent sheet in other Examples and Comparative Examples.

For the backsheet, used was white polyethylene film having a basis weight of 22.5 g/m$^2$. This film was whitened due to inorganic filler added thereto.

The absorbent sheet, the second intermediate sheet, the first intermediate sheet and the topsheet were stacked on the backsheet one by one, and then, the sheets were bonded together along the peripheral edge through a hot-melt type adhesive to form an absorbent article, which was taken as Example 1.

Munsell value measured for the body surface of Example 1 was 8.70. In all Examples and Comparative Examples, the Munsell value was determined by using the colorimeter "CR-300", manufactured by MINOLTA Co., Ltd, as set forth above.

Example 2

An absorbent article having a structure similar to that of Example 1 was prepared and taken as Example 2, except that for the topsheet, the first intermediate sheet and the second intermediate sheet, used was spunbonded nonwoven fabric (basis weight: 25 g/m$^2$) manufactured from fibers (2.2 dtex) that were obtained by extruding PP resin into which light blue masterbatch (6.12% by weight of titanium oxide, 3.32% by weight of copper phthalocyanine blue, 1.50% by weight of quinacridone, 89.06% by weight of PP resin) was mixed in an amount of 1.6% by weight. Munsell value was 8.70.

Example 3

An absorbent article was prepared and taken as Example 3, wherein for the topsheet and the first intermediate sheet, used was spunbonded nonwoven fabric (basis weight: 25 g/m$^2$) manufactured from fibers (2.2 dtex) that were obtained by extruding PP resin into which beige masterbatch (16.65% by weight of titanium oxide, 7.17% by weight of yellow oxide, 3.09% by weight of red oxide of iron, 0.75% by weight of carbon black, 72.34% by weight of PP resin) was mixed in an amount of 1.7% by weight. Munsell value was 7.00.

Example 4

An absorbent article was prepared by omitting the first intermediate sheet from the structure of Example 3 and taken as Example 4. Munsell value was 8.00.

Example 5

An absorbent article having a structure similar to that of Example 4 was prepared and taken as Example 5, except that spunbonded nonwoven fabric manufactured with beige masterbatch to have a basis weight of 30 g/m$^2$ was used for the topsheet. Munsell value was 7.25.

Example 6

An absorbent article having a structure similar to that of Example 3 was prepared and taken as Example 6, except that spunbonded nonwoven fabric manufactured with beige masterbatch to have a basis weight of 30 g/m$^2$ was used for the topsheet and the first intermediate sheet. Munsell value was 5.90.

Example 7

An absorbent article was prepared such that the second intermediate sheet was further added to Example 3, and taken as Example 7. For the second intermediate sheet, used was nonwoven fabric identical to that used for the topsheet and the first intermediate sheet. Munsell value was 5.70.

Comparative Example 1

In Comparative Example 1, the spunbonded nonwoven fabric (basis weight: 25 g/m$^2$) that was used in Example 7, was used for the topsheet, while the spunbonded nonwoven fabric (basis weight: 30 g/m$^2$) that was used for the first intermediate sheet of Example 6, was used for the first intermediate sheet and second intermediate sheet. Munsell value measured for the body surface was 5.50.

Comparative Example 2

Spunbonded nonwoven fabric (basis weight: 25 g/m$^2$) was manufactured from fibers (2.2 dtex) that were obtained by extruding PP resin into which black masterbatch (18.20% by weight of carbon black, 54.40% by weight of PP resin, 27.30% by weight of wax) was mixed in an amount of 4.0% by weight, and used for the topsheet in Comparative Example 2. Munsell value was 3.50.

Comparative Example 3

Comparative Example 3 was prepared to have a structure similar to that of Comparative Example 2, except that the topsheet was formed with liquid passage holes.

These liquid passage holes were dotted over a region extending over the entire length of the topsheet along a longitudinally extending centerline thereof and having a width of 20 mm in a transverse direction crossing the centerline. The liquid passage holes were arranged at a pitch of 3 mm in both the longitudinal and transverse directions, and had a diameter of 1 mm at the open end on the side of the body surface. Munsell value was 4.05.

Comparative Example 4

For the topsheet and the first intermediate sheet in Comparative Example 4, used was nonwoven fabric identical to that used for the topsheet in Comparative Example 2. Munsell value was 2.10.

Comparative Example 5

White spunbonded nonwoven fabric (basis weight: 25 g/m$^2$) was manufactured from fibers (2.2 dtex) that were obtained by extruding PP resin into which titanium oxide was mixed in an amount of 0.5% by weight, and used for the topsheet in Comparative Example 5. Munsell value was 9.60.

<Evaluation of Concealability of Vaginal Discharge and Evaluation of Visibility of Menstrual Blood>

(1) Measurement of Value

Value was measured for the body surface (liquid-receiving surface) of each test sample (Examples and Comparative Examples) before dropping liquid.

(2) Evaluation of Concealability of Artificial Vaginal Discharge

By using the calorimeter, a color difference between a color-difference reference color and the body surface of each test sample was measured as Hunter Δ(Lab) value. An initial color difference measured before dropping liquid was indicated by $\Delta E_0$. On the other hand, a color difference measured after dropping 0.5 ml of distilled water (artificial vaginal discharge) onto the topsheet of each test sample was indicated by $\Delta E_1$. The absolute value of the difference between $\Delta E_0$ and $\Delta E_1$, $|\Delta E_0 - \Delta E_1|$ was taken to represent concealability of artificial vaginal discharge, and stated in Table 1.

As the absolute value $|\Delta E_0 - \Delta E_1|$ decreases, the concealability of artificial vaginal discharge can be enhanced. From the results of next evaluation (3) by monitors stated in Table 1, it is seen that the absolute value $|\Delta E_0 - \Delta E_1|$ is preferably equal to or less than 9, more preferably equal to or less than 8, and particularly when based on Examples, the absolute value $|\Delta E_0 - \Delta E_1|$ is preferably equal to or less than 7.71.

(3) Evaluation of Concealability of Artificial Vaginal Discharge by Monitors

After dropping 0.5 ml of artificial vaginal discharge onto the topsheet of each test sample, concealability was visually evaluated by 10 monitors. Evaluation was conducted at a place having brightness of 76 lux, and the average of visual acuities (including corrected visual acuity) of the monitors was 1.0.

Concealability was evaluated by each monitor according to the five-grade system "very good", "good", "not bad", "not good", "very bad". In Table 1, "○" represents the case where the test sample was evaluated "very good" or "good" by at least 8 monitors, "Δ" represents the case where the test sample was evaluated "very good" or "good" by 6 or 7 monitors, and "X" represents the case other than the cases of "○" and "Δ".

(4) Evaluation of Visibility of Artificial Menstrual Blood

As in the evaluation (2), a color difference between a color-difference reference color and the body surface of each test sample was measured. An initial color difference measured before dropping artificial menstrual blood was indicated by $\Delta E_0$. On the other hand, a color difference measured after dropping 0.5 ml of artificial menstrual blood onto the topsheet of each test sample was indicated by $\Delta E_1$. The absolute value of the difference between $\Delta E_0$ and $\Delta E_1$, $|\Delta E_0 - \Delta E_1|$ was taken to represent visibility of artificial menstrual blood, and stated in Table 1.

Here, the artificial menstrual blood was prepared by dissolving 8 g of carboxymethyl cellulose sodium, 80 g of glycerin, 4 g of sodium hydrogen carbonate, 8 g of Red No. 102, 2 g of Red No. 2, and 2 g of Yellow No. 5 in 1 liter of distilled water.

As the absolute value $|\Delta E_0 - \Delta E_1|$ increases, the visibility of artificial menstrual blood can be enhanced. From the results of next evaluation (5) by monitors stated in Table 1, it is seen that the absolute value $|\Delta E_0 - \Delta E_1|$ is preferably equal to or greater than 43, and particularly when based on Examples, the absolute value $|\Delta E_0 - \Delta E_1|$ is preferably equal to or greater than 44.38.

(5) Evaluation of Visibility of Artificial Menstrual Blood by Monitors

After dropping 0.5 ml of artificial menstrual blood onto the topsheet of each test sample, visibility was visually evaluated by 10 monitors. Evaluation was conducted at a place having brightness of 76 lux, and the average of visual acuities (including corrected visual acuity) of the monitors was 1.0.

Visibility was evaluated by each monitor according to the five-grade system "highly visible", "visible", "not very visible", "hardly visible", "invisible". In Table 1, "○" represents the case where the test sample was evaluated "highly visible" or "visible" by at least 8 monitors, "Δ" represents the case where the test sample was evaluated "highly visible" or "visible" by 6 or 7 monitors, and "X" represents the case other than the cases of "○" and "Δ".

<Result>

Table 1 shows evaluation results of the concealability of vaginal discharge and the visibility of menstrual blood, as well as constructions of Examples and Comparative Examples.

From Table 1, it is seen that Munsell value is required to be in the range of 5.7 to 8.7 in order to improve both the vaginal discharge concealability and the menstrual blood visibility.

TABLE 1

|  | Ex. 1 | Ex. 2 | Ex. 3 | Ex. 4 | Ex. 5 | Ex. 6 | Ex. 7 |
|---|---|---|---|---|---|---|---|
| Topsheet | Pink SB 25 g/m² | Light Blue SB 25 g/m² | Beige SB 25 g/m² | Beige SB 25 g/m² | Beige SB 30 g/m² | Beige SB 30 g/m² | Beige SB 25g/m² |
| 1st Intermediate Sheet | Pink SB 25 g/m² | Light Blue SB 25 g/m² | Beige SB 25 g/m² | — | — | Beige SB 30 g/m² | Beige SB 25 g/m² |
| 2nd Intermediate Sheet | Pink SB 25 g/m² | Light Blue SB 25 g/m² | — | — | — | — | Beige SB 25 g/m² |
| Absorbent Sheet | Wet-laid Spunlaced | Wet-laid Spunlaced | Wet-laid Spunlaced | Wet-laid Spunlaced | Wet-laid Spunlaced | Wet-laid Spunlaced | Wet-laid Spunlaced |
| Backsheet | White PE Film | White PE Film | White PE Film | White PE Film | White PE Film | White PE Film | White PE Film |
| Munsell Color System |  |  |  |  |  |  |  |
| Hue | 10.0RP | 6.6B | 6.9YR | 8.3YR | 6.45YR | 6.4YR | 6.4YR |
| Value | 8.7 | 8.7 | 7 | 8 | 7.25 | 5.9 | 5.7 |
| Chroma | 2.60 | 3.1 | 3.2 | 2.3 | 3.2 | 3 | 3 |
| Concealability of Vagina Discharge |  |  |  |  |  |  |  |
| Evaluation by Monitors | ○ | ○ | ○ | ○ | ○ | ○ | ○ |
| $|\Delta E_0 - \Delta E_1|$ | 7.71 | 7.43 | 5.47 | 6.54 | 5.63 | 4.12 | 3.76 |
| Visibility of Menstrual Blood |  |  |  |  |  |  |  |
| Evaluation by Monitors | ○ | ○ | ○ | ○ | ○ | ○ | ○ |
| $|\Delta E_0 - \Delta E_1|$ | 72.69 | 70.52 | 55.24 | 66.31 | 56.27 | 46.77 | 44.38 |

TABLE 1-continued

|  | Comp. Ex. 1 | Comp. Ex. 2 | Comp. Ex. 3 | Comp. Ex. 4 | Comp. Ex. 5 |
|---|---|---|---|---|---|
| Topsheet | Beige SB 25 g/m² | Black SB 25 g/m² | Black SB 25 g/m², Apertured | Black SB 25 g/m² | White SB 25 g/m² |
| 1st Intermediate Sheet | Beige SB 30 g/m² | — | — | Black SB 25 g/m² | — |
| 2nd Intermediate Sheet | Beige SB 30 g/m² | — | — | — | — |
| Absorbent Sheet | Wet-laid Spunlaced | Wet-laid Spunlaced | Wet-laid Spunlaced | Wet-laid Spunlaced | Wet-laid Spunlaced |
| Backsheet | White PE Film | White PE Film | White PE Film | White PE Film | White PE Film |
| Munsell Color System |  |  |  |  |  |
| Hue | 6.4YR | 0.25Y | 1.25Y | 3.7Y | 4.2Y |
| Value | 5.5 | 3.5 | 4.05 | 2.1 | 9.6 |
| Chroma | 2.7 | 0.6 | 0.5 | 0.2 | 0.2 |
| Concealability of Vagina Discharge |  |  |  |  |  |
| Evaluation by Monitors | ◯ | ◯ | ◯ | ◯ | Δ |
| $|\Delta E_0 - \Delta E_1|$ | 3.51 | 2.53 | 2.79 | 2.03 | 10.62 |
| Visibility of Menstrual Blood |  |  |  |  |  |
| Evaluation by Monitors | Δ | X | X | X | ◯ |
| $|\Delta E_0 - \Delta E_1|$ | 42.31 | 27.12 | 32.05 | 18.41 | 83.24 |

Examples 8 and 9

For Examples 8 and 9, panty liner was prepared by stacking topsheet, intermediate sheet, absorbent sheet and backsheet.

For the topsheet and the intermediate sheet, used was spunbonded nonwoven fabric (basis weight: 30 g/m²) comprising colored polypropylene fibers that were melt extruded after mixture of masterbatch. In a region extending over the entire length of the topsheet along a longitudinally extending centerline thereof and having a width of 20 mm, the topsheet used for Examples 8 and 9 was corrugated at a constant pitch in a transverse direction to have longitudinally extending ribs and valleys. In the corrugated region, moreover, a large number of recesses were regularly formed by pin-embossing. It should be noted that the topsheet was not forcibly apertured by pin-embossing. The ribs were arranged at a pitch of 2 mm in the transverse direction. The recesses due to pin-embossing were arranged along bottoms of the valleys. More specifically, the recessed due to pin-embossing were arranged at a pitch of 2 mm (identical to the pitch of ribs) in the transverse direction and at a pitch of 2.3 mm in the longitudinal direction (in a direction parallel with the valleys). These recesses had a diameter of 0.7 mm, and occupied 8.3% the area of the corrugated region. The topsheet was prepared by pressing the nonwoven fabric between first and second rolls for simultaneously forming the corrugation and the recesses. The first roll was provided with circumferentially extending grooves, which had a width of 1.3 mm and were arranged at an axial pitch of 2 mm, and also provided with pressing pins, which had a diameter of 0.7 mm and were arranged at a circumferential pitch of 2.3 mm between adjacent grooves. The second roll was provided with circumferentially extending ridges, which had a width of 0.3 mm and were arranged at an axial pitch of 2 mm. The nonwoven fabric was pressed between the first and second rolls that were in such a mated condition that the pressing pins of the first roll faced bottoms of grooves formed between adjacent ridges of the second roll. At this time, the temperature of the roll surface was set at 100 to 110° C. and the pressure between the rolls was set at 2450 kPa. As a result, the topsheet having the corrugation and the recesses was produced to have a thickness of 1 mm. On the other hand, the intermediate sheet was provided with neither corrugation nor recesses.

The absorbent sheet was identical to that used in Examples 1 to 7 and Comparative Examples 1 to 5. The absorbent sheet was uncolored.

For the backsheet, used was polyethylene film manufactured from colored polyethylene resin to have a basis weight of 23.5 g/m².

In Examples 8 and 9, hue, value and chroma were measured for the individual sheets before assembling the panty liner, and then, hue, value and chroma were measured again from the side of the topsheet after assembling the panty liner. In either case, hue, value and chroma were the averages of three measurements.

Example 8

The topsheet had hue of 7.8YR, value of 8.6, and chroma of 2.0 according to the Munsell color system.

The intermediate sheet had hue of 6.5YR, value of 7.3, and chroma of 3.2 according to the Munsell color system.

The absorbent sheet had hue of 4.2Y, value of 9.6, and chroma of 0.2 according to the Munsell color system.

The backsheet had hue of 4.4YR, value of 7.7, and chroma of 3.3 according to the Munsell color system.

The finished panty liner had a beige color as viewed from the side of the body surface, wherein hue was 6.4YR, value was 7.3, and chroma was 2.8 according to the Munsell color system.

Example 9

The topsheet had hue of 4.0B, value of 9.5, and chroma of 0.85 according to the Munsell color system.

The intermediate sheet had hue of 4.1B, value of 9.6, and chroma of 0.95 according to the Munsell color system.

The absorbent sheet was identical to that of Example 8.

The backsheet had hue of 7.3B, value of 9.1, and chroma of 2.2 according to the Munsell color system.

The finished panty liner had a light blue color as viewed from the side of the body surface, wherein hue was 7.4B, value was 8.9, and chroma was 2.9 according to the Munsell color system.

In the finished panty liners of Examples 8 and 9, the underlying intermediate sheet and absorbent sheet could be seen through the topsheet. However, the value of the body surface of the panty liner could be set within the desirable range by adjusting the colors of the individual components as set forth above.

The concealability of vaginal discharge and the visibility of menstrual blood were evaluated for Examples 8 and 9 by monitors, as in Examples 1 to 7 and Comparative Examples 1 to 5. As a result, both Examples 8 and 9 were evaluated "◯".

TABLE 2

|  |  | Example 8 (Beige) | Example 9 (Light Blue) |
|---|---|---|---|
| Finished Article | Hue | 6.4YR | 7.4B |
|  | Value | 7.3 | 8.9 |
|  | Chroma | 2.8 | 2.9 |
| Topsheet | Hue | 7.8YR | 4.0B |
|  | Value | 8.6 | 9.5 |
|  | Chroma | 2.0 | 0.85 |
| Intermediate Sheet | Hue | 6.5YR | 4.1B |
|  | Value | 7.3 | 9.6 |
|  | Chroma | 3.2 | 0.95 |
| Absorbent Sheet | Hue | 4.2Y | 4.2Y |
|  | Value | 9.6 | 9.6 |
|  | Chroma | 0.2 | 0.2 |
| Backsheet | Hue | 4.4YR | 7.3B |
|  | Value | 7.7 | 9.1 |
|  | Chroma | 3.3 | 2.2 |

As has been described hereinabove, the absorbent article of the present invention is suitable for use with a colored undergarment that matches in color with the article. Because the body surface of the absorbent article has a Munsell value from 5.7 to 8.7, the absorbent article has an excellent concealability of vaginal discharge, whereas when menstruation begins during wear of the absorbent article, the beginning of menstruation can be sensed by a wearer in an early stage. Accordingly, the absorbent article of the present invention can be suitably used as a substitute for a crotch portion of an undergarment.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A colored absorbent article to be attached to an inner side of an undergarment matching in color with the article, the absorbent article having a body surface for facing the skin of a wearer and a garment surface for facing the inner side of the undergarment, a color given to the absorbent article being visually recognizable from the side of the body surface,
wherein the absorbent article comprises a stack of a plurality of sheets, of which at least one sheet is made of a synthetic resin containing a coloring agent, and the article has a central liquid passage region where liquid passage holes are uniformly distributed such that an area ratio of the liquid passage holes to the central liquid passage region is in a range of 8 to 20%, the central liquid passage region having a constant width and extending alone a centerline of the absorbent article over an entire length of the article.
wherein when measured for the body surface of the absorbent article; both the central liquid passage region and the other regions outside the central liquid passage region have a Munsell value in a range of 5.7 to 8.7.

2. A colored absorbent article as sot forth in claim 1, wherein the plurality of sheets comprises a topsheet appearing on the body surface and a backsheet appearing on the garment surface, wherein the topsheet and the backsheet are of the substantially same size and colored to have an analogous color.

3. A colored absorbent article as set forth in claim 2, wherein the topsheet and the backsheet are transversely outwardly protruded to form wing portions of a predetermined area, at a location spaced apart from longitudinally opposed front and rear end edges of the absorbent article.

4. A colored absorbent article as set forth in claim 2, wherein an adhesive layer for adhering to the undergarment is provided on the backsheet such that the adhesive layer is spaced inwardly apart from any edges of the backsheet.

5. A colored absorbent article as set forth in claim 1, which has a thickness of 0.25 to 3.5 mm, between the body surface and the garment surface.

6. A colored absorbent article as set forth in claim 2, wherein the topsheet is a nonwoven fabric.

7. A colored absorbent article as set forth in claim 1, which is to be used as a panty liner for absorbing vaginal discharge.

* * * * *